United States Patent

Wurzinger et al.

[11] Patent Number: 6,139,580
[45] Date of Patent: Oct. 31, 2000

[54] JOINT ENDOPROSTHESIS

[75] Inventors: Anton Wurzinger, Maria Enzersdorf; Franz Winter, Berndorf, both of Austria

[73] Assignee: IMPLANTECH, Medizintechnik Ges.m.b.H., Maria Enzersdorf, Austria

[21] Appl. No.: 09/118,600

[22] Filed: Jul. 17, 1998

[30] Foreign Application Priority Data

Jul. 18, 1997 [AT] Austria .................................. 1233/97

[51] Int. Cl.[7] .......................................................... A61F 2/38
[52] U.S. Cl. ....................................................... 623/20.26
[58] Field of Search ............................ 623/18.11, 16.11, 623/19.11–19.14, 20.11–20.36

[56] References Cited

U.S. PATENT DOCUMENTS

| | | |
|---|---|---|
| 4,309,778 | 1/1982 | Buechel et al. . |
| 4,340,978 | 7/1982 | Buechel et al. . |
| 4,865,606 | 9/1989 | Rehder ...................................... 623/20 |
| 5,387,240 | 2/1995 | Pottenger et al. ......................... 623/20 |
| 5,683,468 | 11/1997 | Pappas ...................................... 623/20 |
| 5,755,802 | 5/1998 | Gerber ...................................... 623/20 |
| 5,755,804 | 5/1998 | Schmotzer et al. ....................... 623/20 |
| 5,782,923 | 7/1998 | Engelbrecht et al. .................... 623/20 |
| 5,824,096 | 10/1998 | Pappas et al. ............................. 623/20 |
| 5,879,391 | 3/1999 | Slamin ...................................... 623/20 |
| 5,879,392 | 3/1999 | McMinn .................................... 623/20 |
| 5,879,394 | 3/1999 | Ashby et al. .............................. 623/20 |

*Primary Examiner*—V. Millin
*Assistant Examiner*—Tram A. Nguyen
*Attorney, Agent, or Firm*—Ostrolenk, Faber, Gerb & Soffen, LLP

[57] ABSTRACT

A joint endoprosthesis has a first implant component which can be attached to a first epiphysis, and a second implant component which can be attached to a second epiphysis of two epiphyses forming a joint, with the first implant component and the second implant component each having articular surfaces for the formation of a swivel joint, and with a sliding piece being provided that in addition enables a rotational movement and a translational movement of the epiphyses with respect to each other. The joint endoprosthesis is characterized in that the first implant component has a housing that can be embedded in the first epiphysis and anchored in the first epiphysis; a first sliding body is mounted in the housing so as to be rotatable about the axis of rotation; a second sliding body is mounted in the first sliding body so as to be translatable in a direction roughly transverse to the axis of rotation; the second sliding body has a portion that projects out of the housing, and is fitted with an articulation surface against which the second implant component rests; and the second sliding body, by a sliding surface, rests against a mating sliding surface provided on the housing.

21 Claims, 2 Drawing Sheets

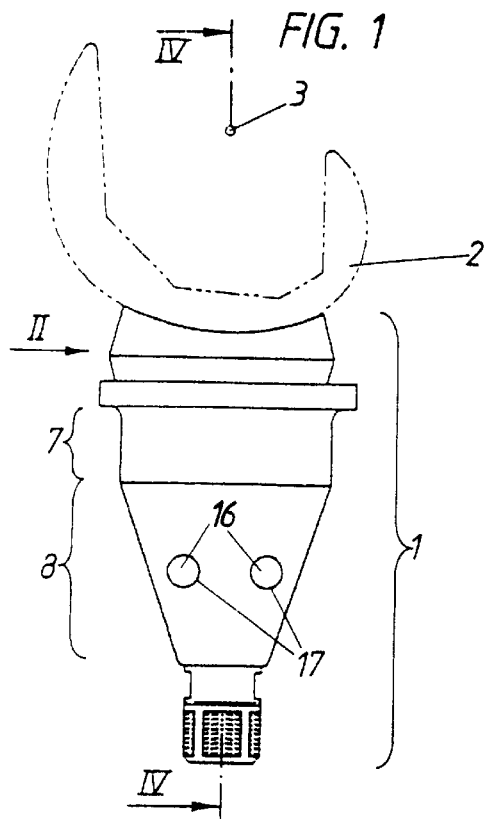
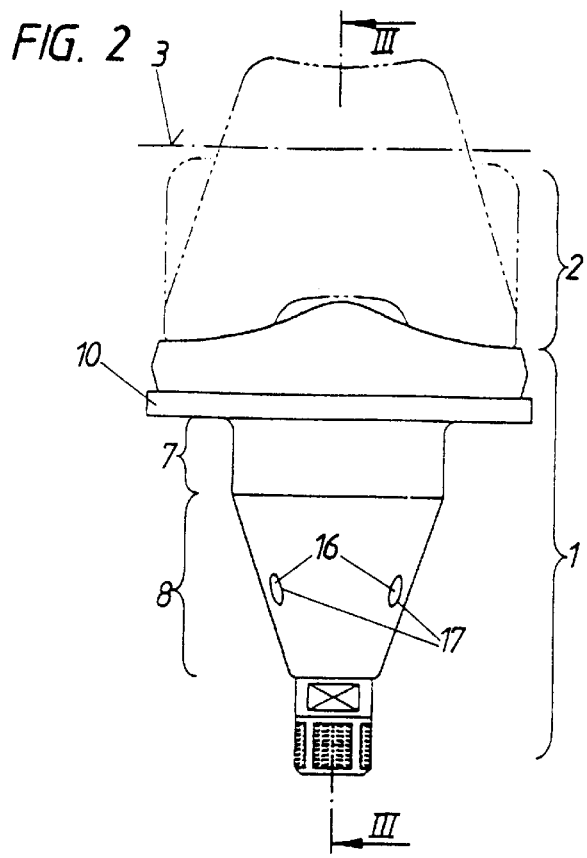
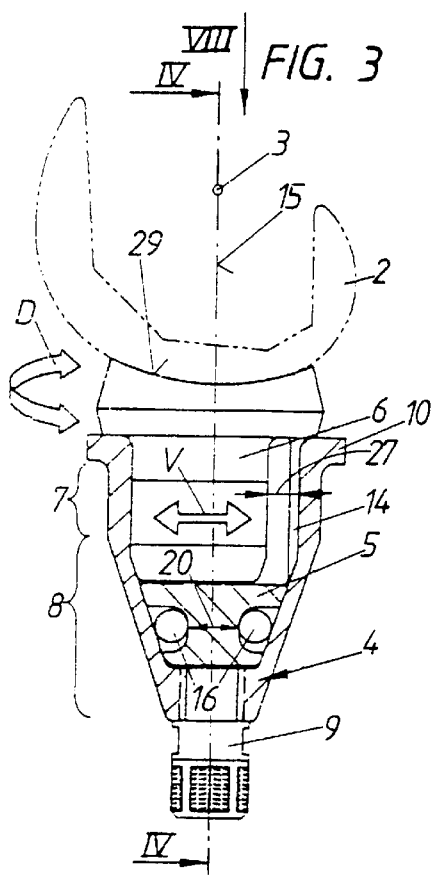
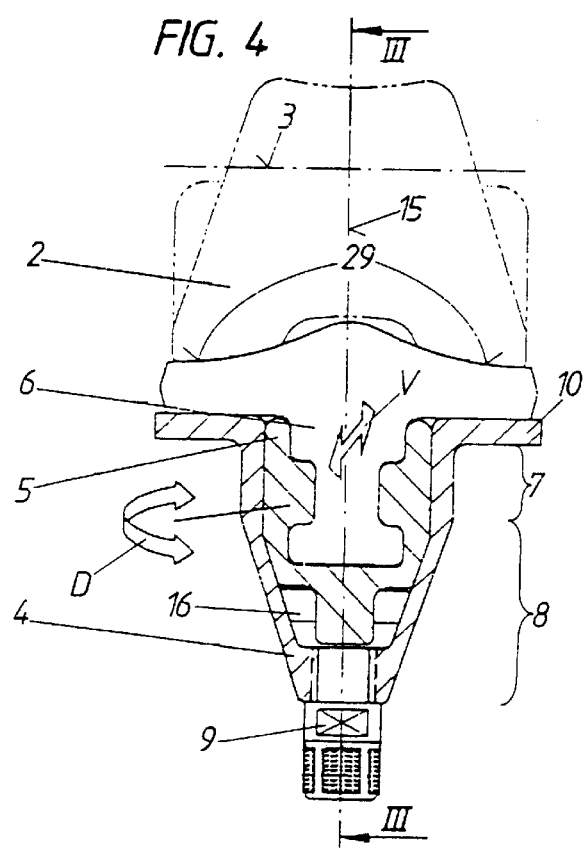

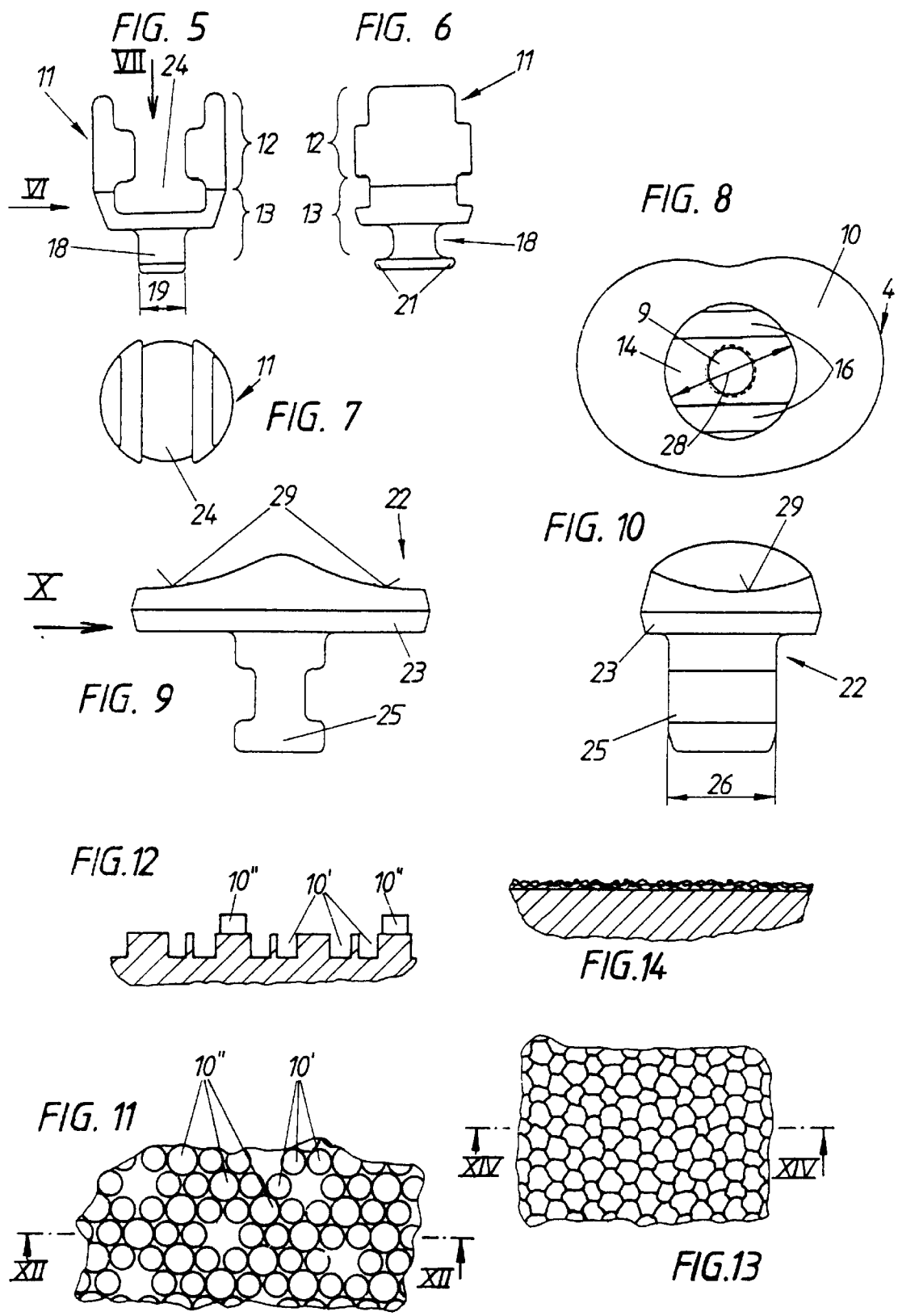

JOINT ENDOPROSTHESIS

BACKGROUND OF THE INVENTION

The invention relates to a joint endoprosthesis, in particular for knee prostheses, which by a first implant component can be attached to a first epiphysis and by a second implant component to a second epiphysis of two epiphyses that form a joint, wherein the first implant component and the second implant component each have articulation surfaces for the formation of a swivel joint enabling swiveling about a swivel axis directed roughly transversally with respect to the longitudinal extent of the first and second bones that have the first and second epiphyses, and which furthermore has a sliding piece which additionally enables a rotational movement and a translational movement of the epiphyses relative to each other, with the rotational movement being about an axis of rotation roughly transversal to the swivel axis and roughly in the longitudinal direction of the first bone and the translational movement being in a plane that is roughly parallel to the swivel axis and roughly transversal with respect to the axis of rotation.

The first generation of serviceable knee joints was fitted with a hinge-type joint. These axial knee joints, whose motion was constrained in cases with very poor axial conditions and extreme ligament instabilities, are in use even to date in limited number. In fact, constrained motion does remedy the instability but it causes substantial disadvantages such as increased stress on the material and above all loosening of the implants from their anchoring in the bone.

A next major generation of knee joints consists of so-called surface prostheses, which merely create new artificial sliding surfaces in cases where wear of cartilage and menisci must be compensated for while the natural system of ligaments and soft parts still maintains the stability of the joint.

The broad application of surface prostheses initially caused a substantial improvement of femoral-tibial joint articulation. This type of prostheses allows the largely preserved ligament system a considerable range of motion of the femoral and tibial sliding surfaces. These are so-called "flat" forms, i.e. sliding surfaces that are configured as flat as possible. Yet, this development at the same time led to severe setbacks in the development of artificial knee prostheses. With all of these prosthesis designs the metal femoral skid in motion only has point-like or linear support on the polyethylene sliding surface of the tibia, an implant material which is indispensable to date. Excessive lump loading of the polyethylene sliding surface often leads to premature destruction of superficial sliding portions as well as of portions lying below the loaded, resulting in more or less markedly increased abrasion conditions which may lead to bone irritation, destruction of bone and dissolution of bone (osteolysis). As a whole, this abrasion phenomenon can be referred to as polyethylene disease, which may induce premature dysfunction of the artificial joint and the bone.

These histological, tribological and clinical recognitions introduced the development of a new generation of artificial knee sliding surfaces. What this development wants to achieve is the provision of new surface structures of the sliding partners and improvement of the anchoring conditions in order to arrest premature loosening of the implants, which arises due to increased abrasion and due to incorrect loading of the implants.

The natural conditions of movement of the knee joint are complex and cannot be imitated completely by artificial constructions. The dominant flexion and extension movements in a complex manner are connected with motions of rotation whose center of rotation shifts constantly, namely due to the one sliding partner being dislocated in anterior-posterior direction (AP) by the so-called rolling-sliding movement. This complex biomechanical motion is constantly influenced by additional factors such as conditions of the ligament system in lateral and in AP direction as well as of the articular capsule, muscular tension, patella tension and above all the axial changes of the bone geometry of the femur and tibia.

The efforts of the current generation of knee joints are moving away from the "flat" forms in favor of the more conformal types, since low conformality leads to excessive „contact stress" of the polyethylene, which in turn causes increased abrasion. Increased conformality on the other hand carries in it the danger of limiting the motion. After all, the rotation and gliding movements in AP direction are not to differ too much from the natural conditions. Current efforts are directed toward achieving a high level of conformality without limiting the rotational and gliding movements. There already are functioning knee joints (U.S. Pat. No. 4,340,978 and U.S. Pat. No. 4,309,778), which on the one hand allow the rotational movement, so-called "rotating-platform" and on the other hand "artificial menisci", so-called "meniscal bearings", which travel in AP direction on a kind of guiding track mechanism and imitate AP dislocation. The knee joints known from the two above-cited US Letters Patent are complicated in construction in that between the first and the second implant component two sliding bodies are inserted on the first implant component which are arranged at a distance from each other and are guided in tracks on the first implant component and which constitute the articular surfaces for the formation of a swivel joint, which sliding bodies enable both a motion of rotation and a swiveling motion since the guiding tracks are arranged in the shape of an arc. One disadvantage of this is, however, that the guiding tracks lie completely exposed and open toward the joint and that the rotary motions can only be carried out precisely in accordance with the guiding tracks, as a result of which translational motion is no longer possible. However, in accordance with another embodiment according to these US Letters Patent the guiding tracks have very much clearance, thus allowing not only rotational movements but also, to a very limited extent, translational movements, but as a result thereof the rotational movements are entirely uncontrollable and are not orientated according to an axis of rotation. To date, it has not been possible to find a satisfactory way of combining the two motions, namely the rotational movement and the translational movement, since the rotating platform does not travel and the track-guided meniscal motion is not or hardly capable of rotation. In particular, it is not possible to date to carry out translational movements independently of the rotational movement, i.e. in any rotational position.

SUMMARY OF THE INVENTION

The invention aims at avoiding these disadvantages and difficulties and has as its object to provide a joint endoprosthesis of the initially described kind but in which a combination of both the rotational movement and the translational movement is to be feasible in such a manner that even larger amounts of rotational movement can be carried out in a controlled manner and at the same time a sliding movement can also be carried out over a controlled range, namely independently of the rotational movement. In this way, the anchoring or attaching portions of the joint endoprosthesis are to be protected and a long attachment life is to be achieved. Furthermore, it is to be feasible for all compressive, tensile, lateral and thrust forces to be transmitted over a large area and neutralized; peak loads are to be prevented.

According to the invention, this object is achieved in that
that the first implant component has a housing that can be embedded in the first epiphysis and anchored in that first epiphysis,
that in the housing a first sliding body is mounted so as to be rotatable about the axis of rotation,
that in the first sliding body a second sliding body is mounted so as to be translatable in a direction roughly transversal to the axis of rotation,
that the second sliding body projects out of the housing,
that the second sliding body at its portion that projects out of the housing is fitted with an articulation surface against which the second implant component rests by the articulation surface arranged thereupon and
that the second sliding body by a sliding surface rests against a mating sliding surface provided on the housing.

Herein, advantageously, the first sliding body laterally is completely surrounded by the housing and through an opening of the housing that faces away from the first bone can be inserted into the housing or removed from the housing.

To stabilize the joint endoprosthesis it is advantageous that the first sliding body in the direction of the longitudinal extent of the first bone in the housing in the direction of the axis of rotation be secured against removal from the housing, namely suitably by means of a bayonet-type device, which advantageously is characterized in that for axial retainment there are provided two pins extending transversally through the housing and oriented roughly parallel with respect to each other, which extend in a direction roughly parallel to the swivel axis and below which there engages a base part arranged on the first sliding body, wherein the base part in one direction only has a maximum width that corresponds to the distance of the two pins and in a direction roughly at 90° thereto has projections engaging behind the pins.

A preferred embodiment is characterized in that the first sliding body is provided with an undercut groove that is open toward the opening of the housing and that is formed by side walls oriented parallel with respect to each other, which groove extends in the direction of the translatability of the second sliding body relative to the first sliding body, and wherein the second sliding body is provided with a spring designed to correspond to the groove and engages the groove thereby, wherein suitably the groove extends transversally throughout the first sliding body and the spring of the second sliding body, in the direction of the translatability of the second sliding body relative to the first sliding body, has an extent which is shorter than the groove by the extent of the translation path.

For reasons of strength, the first sliding body is advantageously made from metal.

A preferred embodiment is characterized in that the housing has a cylindrical portion of the interior space, said portion extending inward from the opening of the interior space, and adjoining the same in the direction of the bottom of the housing has a conical portion, in particular a frustoconical portion, wherein the housing at its end that extends into the bone advantageously has a supporting anchor for insertion into the medullary cavity, to which preferably an extension anchor can be affixed.

For reasons of strength, the housing is likewise made from metal.

To ensure proper sliding of the second sliding body on the housing, the housing on its side that faces away from the first bone is advantageously provided with a sliding plate projecting radially outward from the housing, wherein the second sliding body suitably is provided with a sliding plate designed so as to have dimensions roughly equal to those of the housing and by that sliding plate rests against the sliding plate of the housing.

For adjustment to the contour of the bone and for the purpose of guiding without any obstacles a ligament, such as e.g. a cruciate ligament, when using the joint endoprosthesis as a knee joint suitably both the sliding plate of the housing and the sliding plate of the second articulation body are of reniform design, with the longitudinal extent of the sliding plate of the housing extending roughly in the direction of the swivel axis.

Preferably, the second sliding body is made from plastics material, in particular from polyethylene.

The preferred use of the joint endoprosthesis is as a knee joint. In that case, the housing can be anchored in the head of the tibia.

For optimum anchoring of the first implant component in the bone, said component has structured surfaces on its external sides facing the bone, wherein particularly the first implant component on that side of the sliding plate by which the latter rests against the epiphysis has a plurality of cylindrical depressions, in particular bores, with diameters of 0.3 to 1 mm, preferably 0.5 to 1 mm, and with depths between 0.3 and 1 mm, preferably 0.5 and 1 mm, such that a porosity of between 50 and 80%, preferably 60 and 70%, is realized. Preferably, in addition to the cylindrical depressions there are cylindrical protuberances having diameters between 0.3 and 1 mm, preferably 0.5 and 1 mm, and heights between 0.3 and 1 mm, preferably 0.5 and 1 mm, with the ratio of the number of the cylindrical protuberances to the number of the cylindrical depressions amounting to 3:7 and with a porosity between 50 and 80%, preferably 60 and 70% being present.

On the non-planar surfaces of the first implant component by which it is in contact with the bone there are provided crater-like structured depressions with depths down to 0.5 mm.

BRIEF DESCRIPTION OF THE DRAWINGS

In the appended drawings, wherein

FIGS. 1 and 2 each show side views of the joint endoprosthesis, namely FIG. 2 according to the arrow II of FIG. 1, and FIGS. 3 and 4 sections through the first implant component, namely FIG. 3 along the line III—III of FIG. 2 and FIG. 4 along the line IV—IV of FIG. 1.

FIG. 5 represents a side view of the first sliding body,

FIG. 6 a view thereof in the direction of the arrow VI of FIG. 5 and

FIG. 7 a top view thereof in the direction of the arrow VII of FIG. 5.

FIG. 8 illustrates a view of the housing in the direction of the arrow VIII of FIG. 3.

FIG. 9 shows a side view of the second sliding body,

FIG. 10 a view in the direction of the arrow X of FIG. 9.

FIGS. 11 and 12 as well as 13 and 14 respectively illustrate different surface structures in top view and in section along the lines XII—XII and XIV—XIV of FIGS. 11 and 13.

DETAILED DESCRIPTION OF THE PREFERRED EMBODIMENT

The joint endoprosthesis of the present invention which is depicted in the drawing is configured as a knee prosthesis. However, in a modified version it could also be used for other joints. It has a first implant component 1 which is anchored in the head of the tibia, either without use of cement or by cementing it in. Together with a second implant component 2 affixable to the femur it forms a swivel joint affording the possibility of a swiveling motion about a swivel axis 3 which corresponds to the swiveling motion of the lower leg relative to the thigh.

The first implant component 1 is essentially formed by three portions, namely a housing 4, a first and a second sliding body 5 and 6. The housing, which is of roughly uniform wall thickness, has a cylindrical portion 7 and a frustoconical portion 8 adjoining the same, which merges into a supporting anchor 9. The housing 4 can be inserted into the head of the tibia with its cylindrical and frustoconical portions 7, 8 completely, either integrally or by screwing-in, with the supporting anchor 9 projecting into the medullary cavity. Optionally, an extension anchor of suitable length can be affixed to the supporting anchor 9, if this should be necessary for reasons of bone structure.

On the upper end of the housing 4, i.e. on the end that faces away from the head of the tibia, the housing 4 has a sliding plate 10 protruding radially outward from the housing 4, of roughly reniform surface geometry. The longitudinal extent of this reniform sliding plate is oriented roughly parallel with respect to the swivel axis 3. The side of the sliding plate 10 that is unencumbered by the tibia is polished, the lower face of the sliding plate, which rests on the head of the tibia, has a structured surface, as is illustrated in FIGS. 11 and 12, with that texture being achieved by means of a plurality of cylindrical bores 10' having diameters ranging from 0.3 to 1 mm, preferably 0.5 to 1 mm, and having depths between 0.3 and 1 mm, preferably 0.5 and 1 mm. Furthermore there are cylindrical protuberances 10", namely with diameters between 0.3 and 1 mm, preferably 0.5 and 1 mm, and heights between 0.3 and 1 mm, preferably 0.5 and 1 mm, with the ratio of the number of the cylindrical protuberances 10" to the number of the cylindrical bores 10' amounting to 3:7. All in all, a porosity between 50 and 80, preferably 60 and 70% is realized in this way. By porosity, it is denoted the percentage of the air volume across a surface area provided with bores and/or protuberances, as compared to the true volume of that surface area.

On the non-planar surfaces, by which the housing 4 is in contact with the bone, there are provided crater-like depressions with depths down to 0.5 mm, as is illustrated in FIGS. 13 and 14.

The housing 4 is made from metal; in particular the following metals can find application here: pure titanium, a titanium cast alloy or a titanium forge alloy or a cobalt chromium alloy.

The housing 4 has a first sliding piece 11 inserted thereinto which has a cylindrical and a frustoconical portion 12 and 13 respectively and the latter portions whereof fit into the cylindrical and frustoconical internal recess 14 of the housing 4, leaving a slight clearance, so that the first sliding piece 11 is rotatable relative to the housing 4, namely about an axis of rotation 15 oriented roughly parallel to the longitudinal axis of the tibia.

This first sliding piece fits entirely into the internal recess 14 of the housing 4 and is secured against dropping from the housing 4 by a bayonet-type locking. This bayonet-type device is realized by two pins 16 extending transversally through the internal recess 14 of the housing, namely through the frustoconical recess of the housing, which are inserted in corresponding bores 17 of the housing 4 and are immobilized in these bores 14, for example by force fit. The longitudinal axes of the pins are located symmetrically with respect to the axis of rotation 15 and are laterally spaced apart therefrom. The first sliding body 11 at its lower end has a base part 18, which in one direction has a maximum width 19 corresponding to the distance 20 of the two pins 16 from each other. In a direction displaced by roughly 90° with respect thereto, the base part 18 has projections 21 which engage behind the pins 16. In this way, the first sliding piece 11 is insertable into the housing 4 only in a very specific rotational position of the first sliding body 11 relative to the housing 4, namely when the base part 18 with its projections 21 is oriented roughly parallel to the pins 16. Upon rotation through a predetermined minimum angle, the projections 21 engage behind the pins 16 and the first sliding piece 11 can no longer be removed from the housing 4 through a movement along the axis of rotation 15. Like the housing, the first sliding body is also made from metal.

The first sliding body 1 serves for receiving a second sliding body 22 therein, which is translatable relative to the first sliding body 11, and thus also relative to the housing 4, namely in a plane oriented roughly parallel to the swivel axis 3 and perpendicular with respect to the axis of rotation 15. The second sliding body 22 also has a sliding plate 23, which, as far as its peripheral shape is concerned corresponds to the sliding plate 10 arranged on the housing 4, hence is also of reniform design. With the second sliding piece 22 inserted in the housing 4, the sliding plate 23 of the second sliding piece 22 rests on the sliding plate 10 of the housing 4. However, in order that in the case of a translational movement the sliding plate 23 of the second sliding body 22 will not project beyond the sliding plate 10 of the housing 4, the sliding plate 23 of the second sliding body 22 in its superficial extent is dimensioned slightly smaller than the sliding plate 10 of the housing 4.

The second sliding body 22 is not only mounted so as to be capable of a translational movement relative to the first sliding body 11 but relative to this latter is also secured against axial removal, namely in the direction of the axis of rotation 15. These two functions are fulfilled by an undercut groove 24 provided in the first sliding body 11, which groove is matched by a correspondingly shaped spring 25 provided on the second sliding body and formed integrally with the sliding plate 23, by which spring the second sliding body is inserted in the groove 24. The translation path of the second sliding body 22 relative to the housing 4 is defined by the longitudinal extent 26 of the spring 25. The longitudinal extent 26 of the spring 25 is designed to be shorter precisely by the desired translational path 27 than the inside diameter 28 of the interior space 14 of the housing 4 (compare FIGS. 3 and 8). The second sliding body 22 thus can at all times be moved only from the stop of the spring 25 on the one side of the housing 4 as far as the stop of the spring 25 on the other side of the housing 4.

The second sliding body 22, which is fabricated from plastics material, preferably from polyethylene, on the upper face of the sliding plate 23, i.e. on the side facing away from the housing 4, has articular cavities 29 for the second implant component 2 that is connected with the femur.

The function of the joint endoprosthesis is explained more fully in the following:

The joint endoprosthesis of the present invention takes into account the natural multicentric motions of the joint, namely in a markedly improved manner compared to previous joint endoprostheses. The motion according to the invention, which is enabled by the joint endoprosthesis, consists in that in the anterior-posterior dislocation movement, which is modeled on the natural sliding movement, a respective new center of rotation arises simultaneously on all of its points of movement and, therefore, the rotation to medial and lateral can simultaneously take place on all such sliding points. This so-called "multiplex motion", which with its dislocation distance acts on the sector of movement of flexion and extension of the main load during walking, has the freedom of rotation necessitated by the needs of the system of soft parts, the bone axis geometry and other individual requirements, in short, the sum of the complex requirements necessary for a given individual knee joint. From this multiplex motion principle there results the possibility of providing the tibial sliding surfaces with a high degree of conformality of the articulation partners of the femoral implant component 2 and tibial implant component I that has not been possible to date. The great conformality of the polyethylene sliding surface of the sliding body 22 gives rise to a maximum of distribution of the compression and thrust forces between the femur implant component 2 and the sliding body 22. In particular, the stress load on the polyethylene sliding surface of the sliding body 22, which arises due to the rolling-sliding movement of AP dislocation, is markedly reduced. The multiple rotational movements on all points of the dislocation path of the tibial sliding surface of the sliding body 22 furthermore absorb the lateral stress movements and thrust movements which otherwise would have to be borne entirely by the anchoring of the tibia.

Summing up, the new multiplex motion sliding principle leads to three essential improvements in the artificial knee joint:
1. Increased conformality of the articulation surface of femur and tibia.
2. Reduction in the stress load on the polyethylene tibial sliding surface.
3. The multiform motion protects the anchoring portions.

The function of the simultaneity of the movement of rotation to medial and lateral as well as of the dislocation movement of anterior-posterior is essential to the invention. This function is transmitted to the second sliding body 22. All compressive, tensile, lateral and thrust forces are transmitted over large areas, i.e. at maximum support of the femur part, i.e. of the second implant component 2, on the second sliding body 22 of the tibia and neutralized due to the multiplex motion principle of the present invention. This distribution of forces prevents point-shape or small-area focal stress loading of the polyethylene and at the same time prevents peak loads on the anchoring of the implants 1, 2 of tibia as well as femur.

The finely polished table-like plain bearing of the second sliding body 22, which conformally corresponds with the second femural implant component 2, allows the necessary rolling and sliding movement in flexion and extension of the joint at maximal area contact, but is retained laterally by virtue of the conformality. The second sliding body 22 itself moves with a large surface on the sliding plate 10 of the housing 4. The forces hence are transmitted from the lower face of the second sliding body 22 to the large sliding plate 10 of the housing 4 over a large area and are not imposed on the lower-lying portions, which merely exert a guiding and retaining function. The novel multiplex motion principle of the present invention aims at a minimum of load on the material above all of the tibial implant component 1. One of the objects achieved by means of the present invention consists in reducing polyethylene disease, another object which has also been achieved consists in protecting the anchoring in order to prevent early loosening of the implants which limits the life thereof.

What is claimed is:

1. Joint endoprosthesis, which by a first implant component (1) can be attached to a first epiphysis and by a second implant component (2) to a second epiphysis of two epiphyses that form a joint, wherein the first implant component (1) and the second implant component (2) each have articulation surfaces for the formation of a swivel joint enabling swiveling about a swivel axis (3) directed roughly transversally with respect to the longitudinal extent of the first and second bones that have the first and second epiphyses, and which furthermore has a sliding piece (11, 22) which additionally enables a rotational movement (D) and a translational movement (V) of the epiphyses relative to each other, with the rotational movement (D) being about an axis of rotation (15) roughly transversal to the swivel axis (3) and roughly in the longitudinal direction of the first bone and the translational movement (V) being in a plane that is roughly parallel to the swivel axis (3) and roughly transversal with respect to the axis of rotation (15), characterized in that the first implant component (1) has a housing (4) that can be embedded in the first epiphysis and anchored in that first epiphysis, that in the housing (4) a first sliding body (11) is mounted so as to be rotatable about the axis of rotation (15), that in the first sliding body (11) a second sliding body (22) is mounted so as to be translatable in a direction roughly transversal to the axis of rotation (15), that the second sliding body (22) projects out of the housing (4), that the second sliding body (22) at its portion that projects out of the housing (4) is fitted with an articulation surface (29) against which the second implant component (2) rests by the articulation surface arranged thereupon and that the second sliding body (22) by a sliding surface rests against a mating sliding surface provided on the housing (4).

2. Joint endoprosthesis according to claim 1, characterized in that the first sliding body (11) laterally is completely surrounded by the housing (4) and through an opening of the housing (4) that faces away from the first bone can be inserted into the housing (4) or removed from the housing (4).

3. Joint endoprosthesis according to claim 1, characterized in that the first sliding body (11) in the direction of the longitudinal extent of the first bone in the housing (4) in the direction of the axis of rotation (15) is secured against removal from the housing (4).

4. Joint endoprosthesis according to claim 3, characterized in that axial retainment is realized by means of a bayonet-type device (16, 18).

5. Joint endoprosthesis according to claim 4, characterized in that for axial retainment there are provided two pins (16) extending transversally through the housing (4) and oriented roughly parallel with respect to each other, which extend in a direction roughly parallel to the swivel axis (3) and below which there engages a base part (18) arranged on the first sliding body (11), wherein the base part in one direction only has a maximum width (19) that corresponds to the distance (20) of the two pins (16) and in a direction roughly at 90° thereto has projections (21) engaging behind the pins (16).

6. Joint endoprosthesis according to claim 1, characterized in that the first sliding body (11) is provided with an undercut groove (24) that is open toward the opening of the housing (4) and that is formed by side walls oriented parallel with respect to each other, which groove (24) extends in the direction of the translatability of the second sliding body (22) relative to the first sliding body (11), and wherein the second sliding body (22) is provided with a spring (25) designed to correspond to the groove (24) and engages the groove (24) thereby.

7. Joint endoprosthesis according to claim 6, characterized in that the groove (24) extends transversally throughout the first sliding body (11) and that the spring (25) of the second sliding body (22), in the direction of the translatability of the second sliding body (22) relative to the first sliding body (11), has an extent which is shorter than the groove (24) by the extent of the translation path (27).

8. Joint endoprosthesis according to claim 1, characterized in that the first sliding body (11) is made from metal.

9. Joint endoprosthesis according to claim 1, characterized in that the housing (4) has a cylindrical portion (7) of the interior space, said portion extending inward from the opening of the interior space, and adjoining the same in the direction of the bottom of the housing has a conical portion (8).

10. Joint endoprosthesis according to claim 1, characterized in that the housing (4) at its end that extends into the tibia has a supporting anchor (9) for insertion into the medullary cavity.

11. Joint endoprosthesis according to claim 1, characterized in that the housing (4) is made from metal.

12. Joint endoprosthesis according to claim 1, characterized in that the housing (4) on its side that faces away from the first bone is provided with a sliding plate (10) projecting radially outward from the housing.

13. Joint endoprosthesis according to claim 12, characterized in that the second sliding body (22) is provided with a sliding plate (23) said sliding plate (23) resting against the sliding plate (10) of the housing (4).

14. Joint endoprosthesis according to claim 12, characterized in that both the sliding plate (10) of the housing (4) and the sliding plate (23) of the second sliding body (22) are of reniform design, with the longitudinal extent of the sliding plate (10) of the housing (4) extending roughly in the direction of the swivel axis (3).

15. Joint endoprosthesis according to claim 1, characterized in that the second sliding body (22) is made from plastics material, in particular from polyethylene.

16. Joint endoprosthesis according to 1, characterized in that the housing (4) can be anchored in the head of the tibia.

17. Joint endoprosthesis according to claims 1, characterized in that the first implant component (1) has structured surfaces on its external sides facing the tibia.

18. Joint endoprosthesis according to claim 17, characterized in that the first implant component (1) on the non-planar surfaces by which it is in contact with the bone has crater-like structured depressions with depths down to 0.5 mm (FIG. 13, 14).

19. Joint endoprosthesis according to claim 1, wherein said endoprosthesis is a knee prosthesis.

20. Joint endoprosthesis according to claim 9, wherein said conical portion is a frustoconical portion.

21. Joint endopr6sthesis according to claim 10, wherein an extension anchor is affixed to said supporting anchor.

\* \* \* \* \*